(12) United States Patent
Tanno et al.

(10) Patent No.: US 10,272,727 B2
(45) Date of Patent: Apr. 30, 2019

(54) PNEUMATIC TIRE

(71) Applicant: The Yokohama Rubber Co., LTD., Minato-ku, Tokyo (JP)

(72) Inventors: Atsushi Tanno, Hiratsuka (JP); Hayato Sakamoto, Hiratsuka (JP)

(73) Assignee: The Yokohama Rubber Co., LTD. (JP)

( * ) Notice: Subject to any disclaimer, the term of this patent is extended or adjusted under 35 U.S.C. 154(b) by 391 days.

(21) Appl. No.: 15/024,777

(22) PCT Filed: Apr. 15, 2014

(86) PCT No.: PCT/JP2014/060736
§ 371 (c)(1),
(2) Date: Mar. 24, 2016

(87) PCT Pub. No.: WO2015/045460
PCT Pub. Date: Apr. 2, 2015

(65) Prior Publication Data
US 2016/0243904 A1     Aug. 25, 2016

(30) Foreign Application Priority Data
Sep. 24, 2013  (JP) .................................. 2013-196856

(51) Int. Cl.
*B60C 19/00*  (2006.01)
*B60C 5/00*  (2006.01)
(Continued)

(52) U.S. Cl.
CPC ........ *B60C 19/002* (2013.01); *B29D 30/0061* (2013.01); *B29D 30/0681* (2013.01);
(Continued)

(58) Field of Classification Search
CPC ..... B60C 19/00; B60C 19/002; B60C 19/003; B60C 19/12; B60C 19/122; B60C 19/125
See application file for complete search history.

(56) References Cited

U.S. PATENT DOCUMENTS

| 5,611,155 A | 3/1997 | Brown et al. |
| 5,740,620 A | 4/1998 | Giese et al. |

(Continued)

FOREIGN PATENT DOCUMENTS

| JP | H02-071327 | 5/1990 |
| JP | H04-030907 | 7/1992 |

(Continued)

OTHER PUBLICATIONS

International Search Report for International Application No. PCT/JP2014/060736 dated Jul. 22, 2014, 4 pages, Japan.

*Primary Examiner* — Justin R Fischer
(74) *Attorney, Agent, or Firm* — Thorpe North & Western

(57) ABSTRACT

The present technology provides a pneumatic tire having a mechanical fastener member for attaching an object with specific functionality to an inner surface of the pneumatic tire, particularly, a pneumatic tire such that, as the pneumatic tire rolls, the object with the specific function attached by the mechanical fastener member can be effectively prevented from executing rotating motion about the mechanical fastener member as a rotation central axis. The pneumatic tire of the present technology has a first member of a mechanical fastener separable into two members, disposed on the tire inner surface. On the tire inner surface around the mechanical fastener member, a recessed flat surface region is formed as a recessed portion having a step from peripheral portions of the recessed portion.

12 Claims, 9 Drawing Sheets

(51) Int. Cl.
  *B60C 17/04*   (2006.01)
  *B60C 23/04*   (2006.01)
  *B29D 30/00*   (2006.01)
  *B29D 30/06*   (2006.01)
  *B60C 17/00*   (2006.01)
  *G01N 21/33*   (2006.01)

(52) U.S. Cl.
  CPC .............. *B60C 17/00* (2013.01); *B60C 17/04* (2013.01); *B60C 19/00* (2013.01); *B60C 19/003* (2013.01); *B60C 23/0493* (2013.01); *G01N 21/33* (2013.01); *B29D 30/0662* (2013.01); *B29D 2030/0072* (2013.01); *B29D 2030/0083* (2013.01); *B29D 2030/0683* (2013.01); *B60C 2019/004* (2013.01)

(56) References Cited

U.S. PATENT DOCUMENTS

| | | |
|---|---|---|
| 2003/0155054 A1 | 8/2003 | Bell |
| 2006/0260726 A1 | 11/2006 | Bell |
| 2010/0108222 A1 | 5/2010 | Bell |
| 2011/0113630 A1 | 5/2011 | Bell |
| 2011/0290395 A1 | 12/2011 | Tanno et al. |
| 2012/0024439 A1 | 2/2012 | Tanno et al. |
| 2012/0298272 A1 | 11/2012 | Tanno et al. |

FOREIGN PATENT DOCUMENTS

| | | |
|---|---|---|
| JP | H11-0164722 | 6/1999 |
| JP | 2000-514339 | 10/2000 |
| JP | 2005-517581 | 6/2005 |
| JP | 2006-044503 | 2/2006 |
| JP | 2012-025318 | 2/2012 |
| JP | 2012-025319 | 2/2012 |
| JP | 2012-240465 | 12/2012 |
| JP | 2012-240603 | 12/2012 |
| WO | WO 1996/01061 | 1/1996 |
| WO | WO 1998/02057 | 1/1998 |
| WO | WO 2003/070496 | 8/2003 |
| WO | WO 2008/0133093 | 11/2008 |

PNEUMATIC TIRE

TECHNICAL FIELD

The present technology relates to a pneumatic tire.

More specifically, the present technology relates to a pneumatic tire provided with a mechanical fastener member for attaching an object with specific functionality to an inner surface of the pneumatic tire, particularly a pneumatic tire such that, as the pneumatic tire rolls, the object with the specific function attached by the mechanical fastener member can be prevented from executing rotating motion about the mechanical fastener member as a rotation central axis.

BACKGROUND ART

In recent years, various attempts at disposing objects having various functions on an inner circumferential surface and the like of a pneumatic tire have been made.

For example, an attaching method has been proposed in which tire tags (radio frequency identification tags, for example), chips, or the like are attached to an inner liner or the like of a green tire using a so-called surface fastener such as a hook and loop fastener or a hook and hook fastener (see Japanese Unexamined Patent Application Publication No. 2005-517581A).

Additionally, a pneumatic tire has been proposed in which a surface fastener is vulcanization bonded to a region corresponding to a tread portion of a tire inner surface, and a noise absorbing member is attached to the tire inner surface via the surface fastener (see Japanese Unexamined Patent Application Publication No. 2006-044503A).

The surface fasteners proposed in Japanese Unexamined Patent Application Publication Nos. 2005-517581 and 2006-044503A are preferable in that a relatively strong engagement force is realized when attaching an object, and engagement on a surface can be achieved without slight misalignments becoming a problem during attachment.

However, with surface fasteners, a state in which the individual engaging elements of the surface fastener are engaged is not ideal due to the inner circumferential surface of the pneumatic tire being an annular, curved surface. With surface fasteners, portions of the edges and center portions become raised, and an amount of obtained engagement force varies (positional variation within the tire and variation from tire to tire). As a result, in some cases, the expected engagement force is not obtained. Additionally, partial physical deterioration and deterioration/declining over time of the engagement force of an entirety of the surface fastener accompanying the progression of the partial physical deterioration occur as a result of repetitive deformation and compaction over an extended period of time caused by rolling motion at high speeds in a state of relatively elevated temperatures. This has led to cases in which difficulties have been met in maintaining a desired engagement force over an extended period of time.

Furthermore, while it may be said that the surface fastener is preferable in that engagement on a surface is achieved without slight misalignments and the like becoming a problem during attachment, when the attached object with functionality is a precision measurement instrument or the like, the attached position needs to be more accurate and precise. From such a viewpoint, there are objects with functionality not geared toward attachment by a surface fastener.

Meanwhile, the present inventors have previously proposed joining a mechanical fastener called a hook or a snap to a tire inner surface and attaching various objects having a desired function via the mechanical fastener (see Japanese Unexamined Patent Application Publication Nos. 2012-25318A, 2012-25319A or 2012-240465A) as a pneumatic tire in which an obtained engagement force is great and essentially free of variations (positional variation within the tire and variation from tire to tire); the engagement force deteriorates/declines minimally over time due to extreme usage conditions including repetitive deformation and compaction over an extended period of time caused by tire rolling motion at high speeds in a state of relatively elevated temperatures; and the desired engagement force can be maintained over an extended period of time.

Specifically, as described in the claims of Japanese Unexamined Patent Application Publication No. 2012-25318A as a representative, the inventors have previously proposed a pneumatic tire having a first fastener of a separable pair of mechanical fasteners, such as a hook or a snap, disposed on a tire inner surface (claims of Japanese Unexamined Patent Application Publication No. 2012-25318A (claim 1)). More specifically, the inventors have previously proposed a pneumatic tire, wherein the first fastener is made of at least two components, the two components being fixed and forming the first fastener by sandwiching a tire member or a tire reinforcing member (claims of Japanese Unexamined Patent Application Publication No. 2012-25318A (claim 2)).

According to the method of joining a mechanical fastener called a hook or a snap to a tire inner surface and attaching a desired object described in Japanese Unexamined Patent Application Publication Nos. 2012-25318A, 2012-25319A or 2012-240465A, it is possible to engage and attach the object to the tire inner surface via the mechanical fastener. Then, according to the method, generally the obtained engagement force is great and free of variations (positional variation within the tire and variation from tire to tire), and the object can be attached in a predetermined position with favorable accuracy. As a result, a pneumatic tire having minimal deterioration/declining over time of the engagement force as a result of extreme usage conditions repeated over an extended period of time, and the capability of maintaining the desired engagement force over an extended period of time was achieved. Moreover, a superior pneumatic tire capable of causing the desired object with a specific function to exhibit the function with favorable accuracy over an extended period of time was achieved.

In particular, when the first member of the mechanical fastener attached to the tire inner surface is a fastener having at least two components, the two components being fixed and forming the first fastener by sandwiching a tire member or a tire reinforcing member, the fixed state is even more robust, resulting in an even more superior mechanical fastener having favorable durability.

However, the pneumatic tire according to the above method is a tire having an object with a specific functionality attached by essentially one mechanical fastener and, as the tire rolls at high speed, the object with a specific functionality attached to a tire lumen may rotate about the mechanical fastener as a rotation central axis. Then, when such a rolling motion is started, the rolling motion may give rise to failure, damage, or the like of the object with a specific functionality, making it no longer possible to continue accurate measurement.

SUMMARY

In view of such points as described above the present technology provides a pneumatic tire having a mechanical fastener member for attaching an object with specific functionality to an inner surface of the pneumatic tire, particularly a pneumatic tire such that, as the pneumatic tire rolls, the object with the specific function attached by the mechanical fastener member can be effectively prevented from executing rotating motion about the mechanical fastener member as a rotation central axis.

A pneumatic tire of the present technology has the configuration described in (1) below.

(1) A pneumatic tire having a first member of a mechanical fastener separable into two members, disposed on a tire inner surface, wherein a recessed flat surface region is formed on the tire inner surface around the mechanical fastener member as a recessed portion having a step from peripheral portions of the recessed portion.

The pneumatic tire according to the present technology preferably is configured as described in any of (2) to (8) below.

(2) A pneumatic tire described in (1) above, wherein the step is at least 0.5 mm in a vertical direction of the tire inner surface, and a distance between a center of the mechanical fastener member and a profile line of the recessed flat surface region is not constant but changes in a plan view of the tire inner surface from the vertical direction.

(3) A pneumatic tire described in (1) or (2) above, wherein the profile shape of the recessed flat surface region is asymmetrical with respect to one and/or both of a line in a tire axial direction and a line in a tire circumferential direction that pass through the center of the mechanical fastener member in a plan view of the tire inner surface from the vertical direction.

(4) A pneumatic tire described in any of (1) to (3) above, wherein the profile shape of the recessed flat surface region is configured by curved lines having a radius of curvature of at least 2 mm or straight lines, without having sharp corners, in a plan view of the tire inner surface from the vertical direction.

(5) A pneumatic tire described in any of (1) to (4) above, wherein the profile shape of the recessed flat surface region is symmetrical with respect to at least one axis of orthogonal coordinates in the tire circumferential direction and the tire axial direction about the mechanical fastener member as the center, and is a shape configured by substantially arcuate shapes and straight lines, in a plan view of the tire inner surface from the vertical direction.

(6) The pneumatic tire described in any of (1) to (5) above, further including an attached object provided with a second member of the mechanical fastener that engages with the first member of the mechanical fastener on the tire inner surface, wherein the object is fixed on the tire inner surface by engaging the two members.

(7) The pneumatic tire described in (6) above, wherein a rotatable angle of the attached object about the mechanical fastener member as the central axis is 10 degrees or less in a plan view of the tire inner surface from the vertical direction.

(8) The pneumatic tire described in (6) or (7), wherein the object provided with the second member is one or a combination of (a) an electronic circuit including a sensor, (b) a balance weight, (c) a run-flat core, (d) an object on which an oxygen scavenger, a drying agent, and/or an ultraviolet light detecting color fixing agent is applied or mounted, (e) and a noise absorbing member.

According to the present technology of (1), it is possible to provide a pneumatic tire having a mechanical fastener member for attaching an object with specific functionality to an inner surface of the pneumatic tire, a pneumatic tire such that, as the pneumatic tire rolls, the object with the specific function attached by the mechanical fastener member can be effectively prevented from executing rotating motion about the mechanical fastener member as a rotation central axis.

With a pneumatic tire of the present technology according to any one of (2) to (5), it is possible to provide a superior pneumatic tire capable of more clearly exhibiting the effects of the pneumatic tire of the present technology according to (1) described above.

With a pneumatic tire of the present technology according to (6) or (7), it is possible to provide a pneumatic tire having a desired object attached to the tire inner surface and effectively prevent the object from executing rotating motion about the mechanical fastener member as a rotation central axis.

With a pneumatic tire of the present technology according to (8), it is possible to provide a pneumatic tire having an object with functionality with a desired function attached to the tire inner surface and effectively prevent the object from executing rotating motion about the mechanical fastener member as a rotation central axis. As a result, it is possible to provide a pneumatic tire capable of favorably achieving the desired object of exhibiting a specific function of the object with favorable accuracy in the pneumatic tire.

BRIEF DESCRIPTION OF DRAWINGS

FIG. 2A is a magnified perspective view of main components illustrating a vicinity of a mechanical fastener member provided on a tire inner surface, and FIG. 2B is a longitudinal sectional model drawing of an area near the same vicinity.

FIG. 3A is a model drawing illustrating an example of a method of manufacturing the pneumatic tire of the present technology in which a bladder is used with a collar member filling a space formed between a protruding tip end portion of the mechanical fastener member and the tire inner surface around the mechanical fastener member, around the mechanical fastener member to be fixed to the tire inner surface, during tire vulcanization molding, and FIG. 3B illustrates a state where a recessed flat surface region has been formed on the tire inner surface after vulcanization molding has been completed.

DETAILED DESCRIPTION

A detailed explanation of the pneumatic tire of the present technology will be given below.

Figure 1:
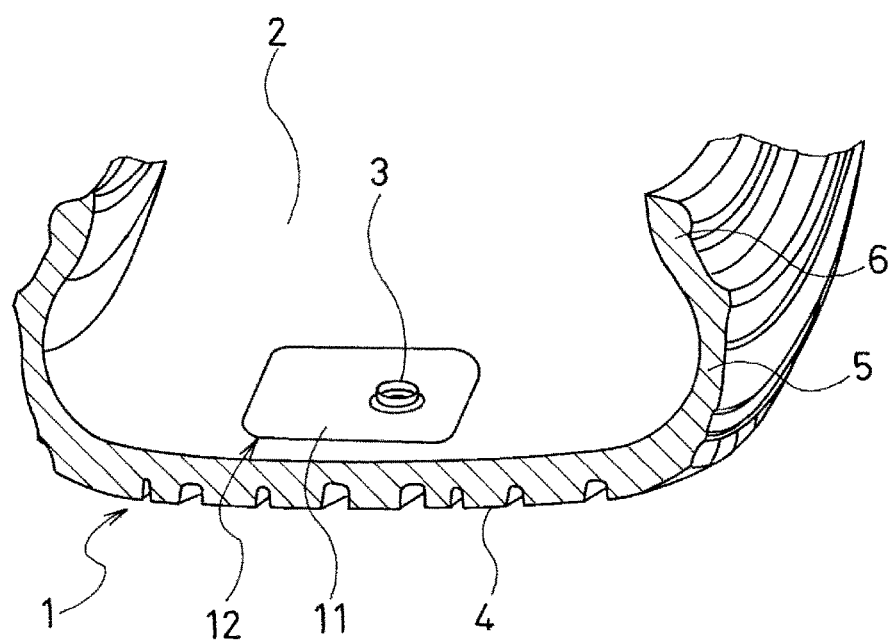
FIG. 1 is a partial breakdown cross-sectional perspective view illustrating an embodiment of the pneumatic tire of the present technology.

As illustrated in FIG. 1, a pneumatic tire 1 of the present technology comprises a mechanical fastener member 3 that is a first fastener member 3 of a mechanical fastener separable into two members, disposed on a tire inner surface 2, wherein a recessed flat surface region 11 is formed on a tire inner surface around the mechanical fastener member 3 as a recessed portion having a step from peripheral portions of the recessed portion. In FIG. 1, 4 is a tread portion, 5 is a side wall portion, and 6 is a bead portion. 12 denotes a profile line of the aforementioned recessed flat surface region 11, and the profile line specifies a profile shape.

While the present technology is based on the premise that a specific object is to be attached to the tire inner surface via the mechanical fastener member 3, the tire inner surface 2 has curvature and therefore, when the object to be attached has a flat bottom surface, interference occurs between the tire inner surface 2 and the bottom surface. To avoid this interference, the recessed flat surface region 11 formed as a recessed portion having a step from peripheral portions is formed on the tire inner surface around the mechanical fastener member 3. The existence of this recessed flat surface region 11 remarkably suppresses interference between the tire inner surface and the bottom surface of the object.

With the suppression of the aforementioned interference, it is possible to favorably prevent the object fixed to the mechanical fastener member 3 from rotating due to a lateral force from the tire inner surface.

Figure 2A:
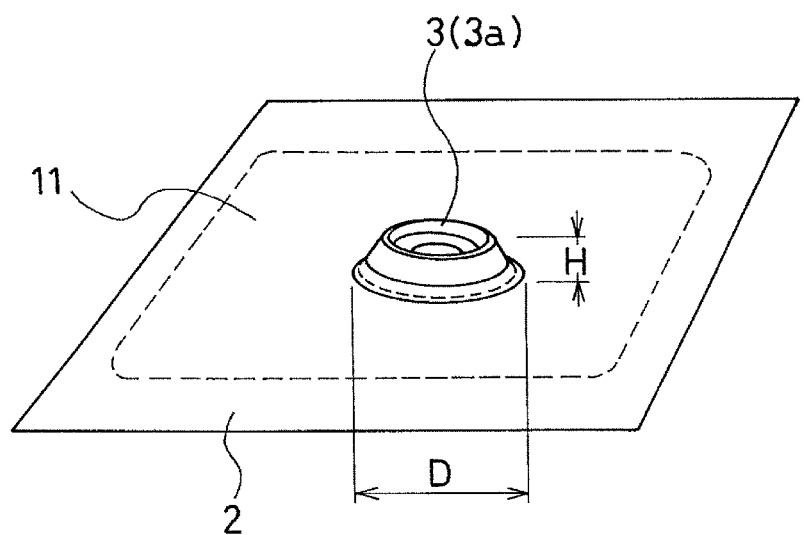
FIGS. 2A and 2B illustrate an embodiment of the pneumatic tire of the present technology.
Figure 2B:
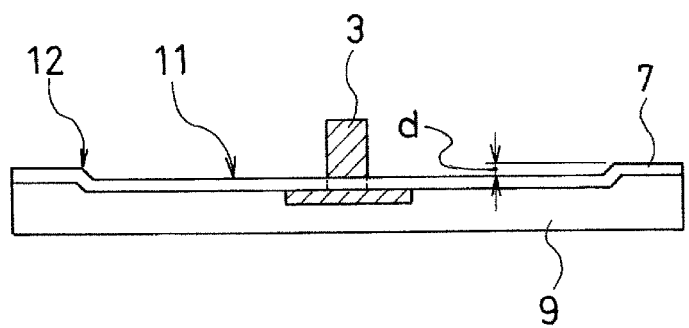
Figure 7A:
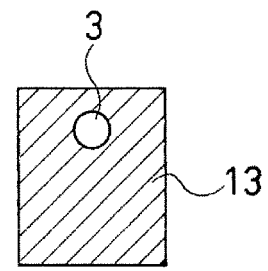
FIG. 7 illustrates an example of a state where an object has been attached to the recessed flat surface region of the present technology.

FIGS. 2A and 2B illustrate an embodiment of the pneumatic tire of the present technology. FIG. 2A is a magnified perspective view of main components illustrating a vicinity of a mechanical fastener member 3 provided on the tire inner surface, and FIG. 2B is a longitudinal sectional model drawing of an area near the same vicinity. Preferably, a bottom portion of the mechanical fastener member 3 is embedded in the tire inner surface 2, and a protruding height H from the tire inner surface and a maximum diameter D of the mechanical fastener member 3 are at least 3 mm and at least 8 mm, respectively. With such an arrangement, the effect of providing a step and forming the recessed flat surface region 11 becomes remarkable. In FIG. 2B, 7 is a tire structural member or a tire reinforcing member, and 9 is an inner liner.

Further, a depth (denoted by d in FIG. 2B) of the step from regions of the peripheral portions of the recessed flat surface region 11 formed as a recessed portion is preferably at least 0.5 mm. An upper limit is preferably about 5 mm. With a large step exceeding 5 mm, vulcanization defects readily occur, and thus such a size is not preferred. Then, additionally, a distance between a center of the mechanical fastener member 3 and the profile line 12 of the recessed flat surface region 11 is preferably not constant, but changes in a plan view of the tire inner surface from a vertical direction. The change in the "distance between a center of the mechanical fastener member 3 and the profile line 12 of the recessed flat surface region 11" refers to a state in which a maximum value and a minimum value of the distance differ by at least 3 mm.

Configuration of the step in such a manner increases the effect of preventing rotation of the attached object fixed by the mechanical fastener member achieved by providing the step. Then, by making the step at least 0.5 mm and further forming an asymmetrical profile shape, it is possible to regulate an attachment orientation (rotation phase) of the attached object, prevent attachment in a wrong orientation, and further suppress rotation of the attached object about the mechanical fastener as a central axis after attachment.

Figures 4A, 4B:
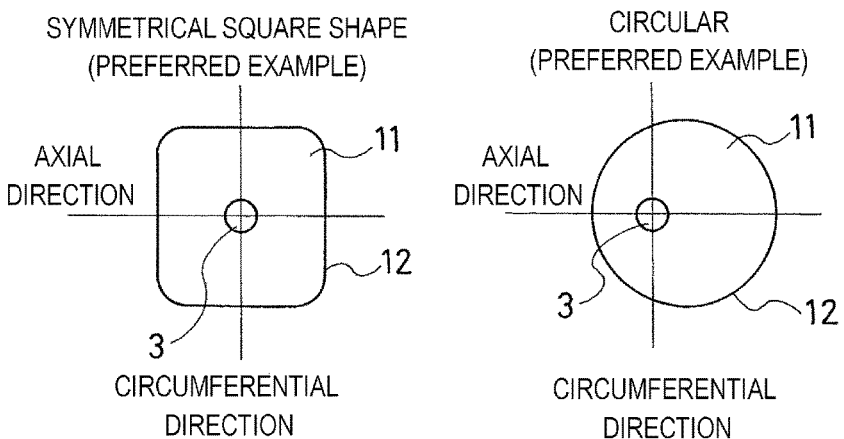
FIGS. 4A to 4C each illustrate an example of a profile shape of the recessed flat surface region of the pneumatic tire of the present technology, FIGS. 4A and 4B satisfying claim 2 and FIG. 4C not satisfying claim 2.
Figure 4C:
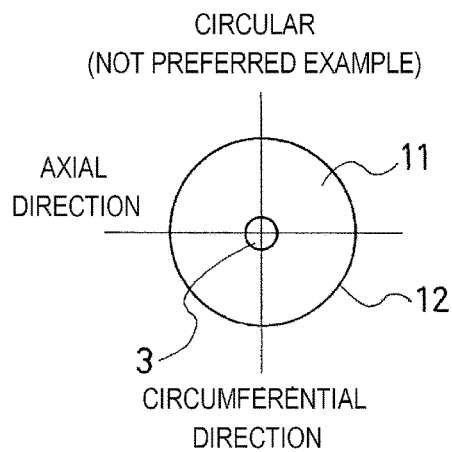
Figures 5A, 5B, 5C, 5D, 5E, 5F:
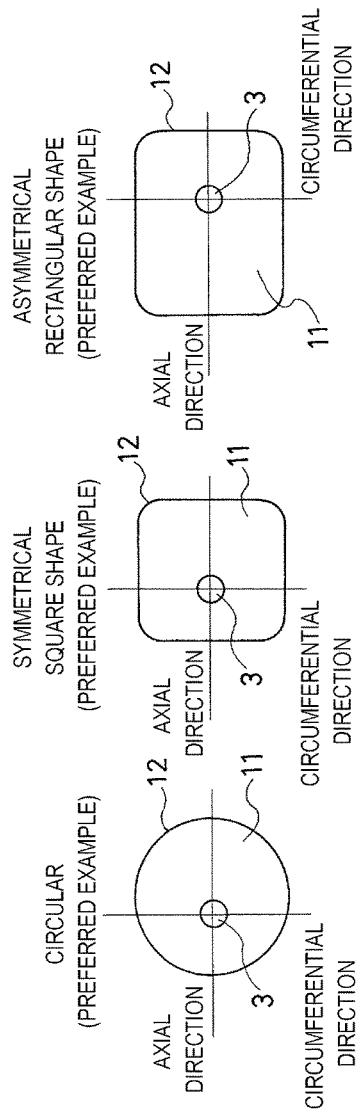
FIGS. 5A to 5F each illustrate an example of the profile shape of the recessed flat surface region of the pneumatic tire of the present technology, FIGS. 5A to 5D satisfying claim 3 and FIGS. 5E and 5F not satisfying claim 3.

Describing the configuration above using FIGS. 4A to 4C, FIGS. 4A to 4C each illustrate an example of a profile shape of the recessed flat surface region 11 of the pneumatic tire of the present technology, with FIGS. 4A and 4B satisfying a requirement of the "change in distance" and FIG. 4C not satisfying the requirement. Accordingly, the profile shapes illustrated in FIGS. 4A and 4B are more preferable than the profile shape illustrated in FIG. 4C.

The pneumatic tire of the present technology may be manufactured by performing vulcanization molding using an especially configured technique.

In particular, the method of forming the recessed flat surface region 11 having the aforementioned profile shape as desired is key, and an outline of the method is described below.

Figure 3A:
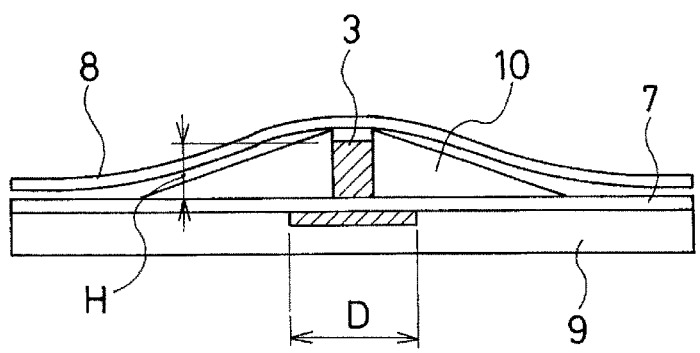
FIGS. 3A and 3B are model drawings illustrating an example of a method of manufacturing the pneumatic tire of the present technology.

That is, as illustrated in FIG. 3A, when the mechanical fastener member 3 is provided in a green tire state and the pneumatic tire is vulcanization molded by a bladder 8, a space having a shape resembling that of a mountain skirt occurs between the bladder 8 and the green tire inner surface due to the existence of a section in which the mechanical fastener member 3 protrudes. A collar member 10 is placed in the space and vulcanization molding is performed. By this vulcanization molding, it is possible to transmit a pressure and a heat of the bladder to an area around a base of the mechanical fastener member 3. Such a base area is then pressed from the collar member 10, forming the recessed flat surface region 11 having the profile line 12 corresponding to a profile line of an external form of the collar member 10 around the mechanical fastener member 3, as illustrated in FIG. 3B.

Figure 3B:
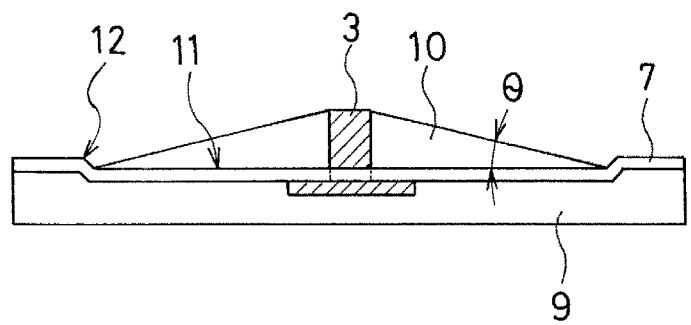

In FIGS. 3A and 3B, 7 is the tire structural member or the tire reinforcing member, and 9 is the inner liner. It is important to form the collar member 10 using a material capable of sufficiently transmitting the pressure and the heat from the bladder to the green tire to be vulcanization molded, and to use a collar member having a flat bottom surface.

The collar member 10 preferably has a cone shape resembling that of a gentle mountain skirt, with the mechanical fastener member 3 as the center (apex). An angle θ of inclination is preferably about from 3 to 20 degrees, but is not limited thereto. The profile shape of the bottom surface matches the profile of the recessed flat surface region 11 to be formed. Further, from the perspective of transmitting the pressure of the bladder to the tire side, the collar member 10 is preferably formed from metals or synthetic resins, molded by laminating release paper, or the like. From the perspective of handling ability, such as ease of removal, the collar member 10 is preferably formed from a fluororesin, such as "Teflon" (registered trademark), according to the findings of the inventors. Further, from the perspective of transmitting the heat of the bladder to the tire side, a heat conductivity is preferably from 0.1 to 300 W/mK.

Further, the profile shape of the recessed flat surface region 11 is asymmetrical with respect to one and/or both of a line in a tire axial direction and a line in a tire circumferential direction that pass through the center of the mechanical fastener member in a plan view of the tire inner surface from the vertical direction. This is to prevent the object with a specific function from being mounted in a wrong attachment orientation at the time of attachment, and a profile shape having a step that allows attachment only in a specific orientation is preferred.

For example, when an electronic device for transmitting and receiving radio waves is to be attached, the device may need to be attached in a specific orientation with respect to the tire structure due to variation in transmission/reception strength of radio waves according to the attachment orientation. In such a case, a profile shape of the form described above is preferred.

Describing the configuration above using FIGS. 5A to 5F, FIGS. 5A to 5F each illustrate an example of the profile shape of the recessed flat surface region 11 of the pneumatic tire of the present technology, with FIGS. 5A to 5D satisfying a requirement of "asymmetric" described above and FIGS. 5E and 5F not satisfying the requirement. Accordingly, the profile shapes illustrated in FIGS. 5A to 5D are more preferable than those illustrated in FIGS. 5E and 5F.

Figure 6:
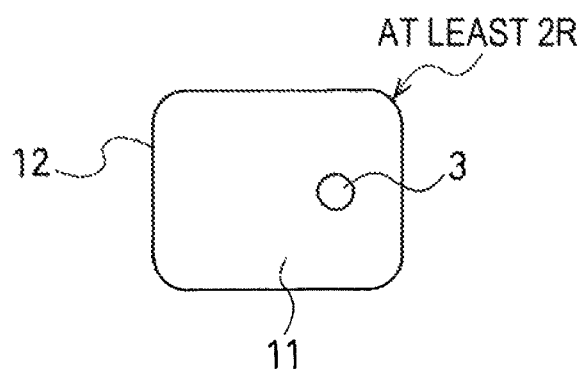
FIG. 6 is a model drawing illustrating an example of the profile shape of the recessed flat surface region of the present technology according to claim 4.

Further, the profile shape of the recessed flat surface region is preferably configured by curved lines having a radius of curvature of at least 2 mm or straight lines, without having sharp corners, in a plan view of the tire inner surface from the vertical direction. FIG. 6 illustrates an example of this form. Sharp corners become starting points for crack occurrence, decreasing tire durability, and are therefore not preferred.

In the present technology, the "mechanical fastener" is a pair of fastener members configured so that two or more fastener members can be separated and can be physically re-engaged, and so that this engaging and separating can be freely repeated, and is basically the same as those described in Japanese Unexamined Patent Application Publication Nos. 2012-25318A, 2012-25319A or 2012-240465A above.

Exemplary types of such a mechanical fastener are those known as "hooks" or "snaps." Specific examples of products in the clothing industry that are generally included as mechanical fasteners are snap buttons, ring snaps, ring hooks, American snaps, American hooks, eyelet hooks, spring hooks, and jumper hooks. Such mechanical fasteners differ from so-called surface fasteners in that while an area of the engaging part of a surface fastener is unlimited in the entire area, the area of the engaging part of a mechanical fastener is small (e.g. preferably from about 1 to 115 $mm^2$ and more preferably from about 4 to 90 $mm^2$). In other words, mechanical fasteners are point fasteners. That is, even when engaged at a small area of from about 1 to 115 $mm^2$, for example, due to a mechanical male-female structure or the like, strong engaging is achieved. Thus, a conventional structure for the mechanical fastener may be used. The mechanical fastener can be formed from materials such as metals, synthetic resins, hard rubbers, and the like.

The advantages of using such a mechanical fastener are basically the same as those described in the prior art.

While in the present technology an area near a tire equator of the tire inner surface such as illustrated in FIG. 1 is given as an example of the attachment position of the mechanical fastener member 3, the present technology is not limited thereto. In such a tread portion 4, a centrifugal force resulting from tire rotation is strongly received, and the shape of the tire inner surface repeatedly changes in association with the rolling motion of the tire. Thus, the attachment position may be provided on the tire inner surface near the bead portion 6 or near the side wall portion 5, which is minimally affected by such factors.

The mechanical fastener member 3 is preferably formed from two or more components 3a, 3b, as illustrated by the exemplary forms in FIGS. 8A, 8B, 9A, and 9B. Then, preferably the two or more components 3a, 3b are integrally fixed, forming the mechanical fastener member 3 by sandwiching the tire member or the tire reinforcing member 7 fixed to the tire, and the mechanical fastener member 3 is fixed to the tire member or the tire reinforcing member 7 fixed to the tire by vulcanization bonding. This is because the mechanical joining force between the components 3a, 3b increases a fixing force to the tire member or the tire reinforcing member 7 fixed to the tire. The two components 3a, 3b are fixed integrally and form the first member of the pair of mechanical fastener members 3. As illustrated in FIG. 2A, primarily the component 3a is exposed on the tire inner surface 2.

Here, the "tire member" refers to a component of the tire made from rubber, resin, or the like, and specifically refers to an inner liner, a carcass, or the like. Alternatively, a rubber layer exclusively for being sandwiched between the component 3a and the component 3b of the fastener, a rubberized reinforcing fiber layer or a resin layer, or a plurality of laminated layers thereof may be provided on the tire inner surface. Such a configuration is preferable because, generally, air shutoff performance in the tire is enhanced.

The collar member used in a vulcanization molding process of the pneumatic tire of the present technology is removed from the tire after vulcanization molding is completed. That is, the collar member does not become a constituent member of the tire during tire use. However, a detachable collar member may be placed in a space formed between a protruding tip end portion of the mechanical fastener member and the tire inner surface surrounding the mechanical fastener member and supplied for distribution and storage of the tire to physically protect the protruding tip end portion of the mechanical fastener member and the mechanical fastener member in its entirety.

In this case, the collar member used during distribution and storage may be used as is in the vulcanization molding process of the pneumatic tire, or may be a separate collar member that is particularly ideal for a protection application during distribution and storage.

In the pneumatic tire of the present technology, the pneumatic tire preferably further includes an attached object with a specific function having a second member of a mechanical fastener that engages with the first member 3 of the mechanical fastener on the tire inner surface, wherein the object is fixed on the tire inner surface by engaging the two fastener members. Such an arrangement is preferred from the perspective of realizing a pneumatic tire having an enhanced function.

In this case, as illustrated in FIG. 7, the profile line shape 12 of the recessed flat surface region 11 is preferably formed so that a rotatable angle of an attached object 13 about the mechanical fastener member 3 as the central axis is 10 degrees or less in a plan view of the tire inner surface from the vertical direction. When the rotatable angle exceeds 10 degrees, contact with the tire inner surface due to rotation of the attached object becomes severe in terms of frequency, impact, speed, and the like, decreasing durability.

Figure 7B:
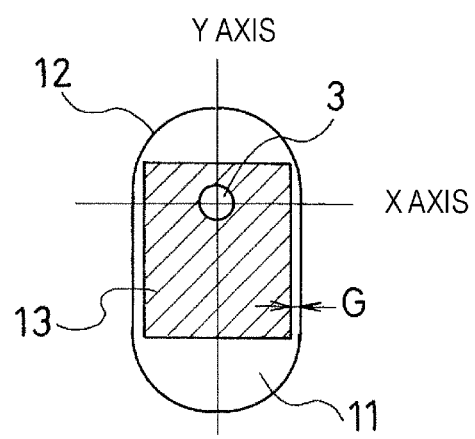
Figure 8A:
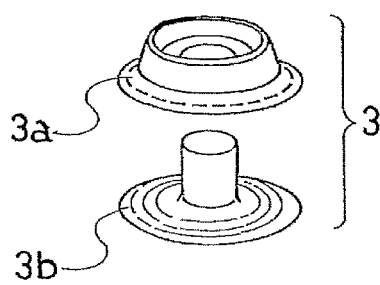
FIGS. 8A and 8B are explanatory drawings illustrating an exemplary shape of a first member of a mechanical fastener separable into two members used in the pneumatic tire of the present technology; and are perspective model drawings of an appearance thereof illustrating that the first member is formed from two components.
Figure 8B:
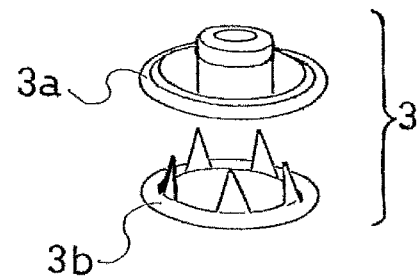
Figure 9A:
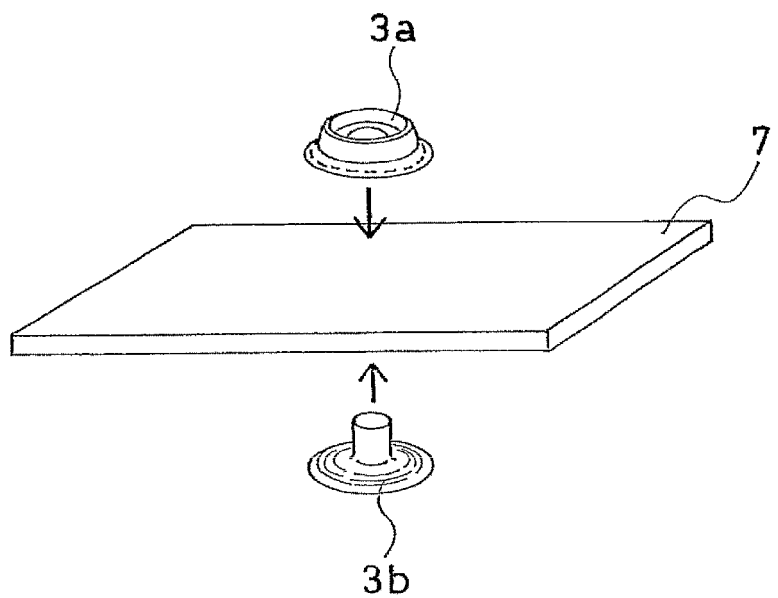
FIGS. 9A and 9B are magnified views of main components illustrating an embodiment of the pneumatic tire of the present technology. Each of the magnified views of main components illustrates a state where the first member includes the two components illustrated in FIGS. 8A and 8B, and the two components are fixed and form the first member by sandwiching a tire member or a tire reinforcing member.
Figure 9B:
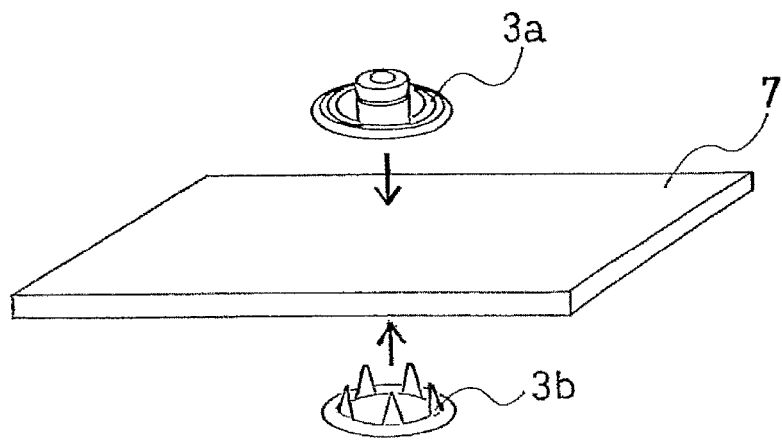

According to the findings of the inventors, a highly versatile, most superior recessed flat surface region is a region having the profile line shape 12 of an athletic track shape such as illustrated in FIG. 7B, and a gap G between the attached object 13 and the profile line 12 that is from 1.0 to 5.0 mm. In other words, the shape is such that semicircles symmetrical with respect to a rectangular central portion are joined on both sides. While the profile line shape 12 is not limited to this shape only, such a shape is an exemplary form in terms of handling ability, workability, versatility, and the like.

The attached object may be selected based on desired characteristics and is not particularly limited, but preferable examples thereof include one or a combination of (a) an electronic circuit including a sensor, (b) a balance weight, (c) a run-flat core, (d) an object on which an oxygen scavenger, a drying agent, and/or an ultraviolet light detecting color fixing agent is applied or mounted, and (e) a noise absorbing member.

EXAMPLES

An explanation of the pneumatic tire of the present technology will be given below on the basis of working examples.

Working Examples 1, 2, Comparative Example 1

Working Examples 1 and 2 and Comparative Example 1 were examined for the presence/absence of rotation of an attached object due to the presence/absence of formation of a recessed flat surface region, and those with such a formation (Working Examples 1, 2) were examined for the presence/absence of rotation of an attached object due to a difference in the depth d of the recessed flat surface region. The recessed flat surface region was formed by performing vulcanization joining on the mechanical fastener while simultaneously using a collar member during vulcanization molding (Working Examples 1, 2). In the samples of Comparative Example 1, a collar member was not used, and the recessed flat surface region was not formed.

The shape of the recessed flat surface region in Working Examples 1 and 2 in the plan view was an athletic track shape as illustrated in FIG. 7B. The tire of Working Example 1 had a depth d of the recessed flat surface region of 0.3 mm, and the tire of Working Example 2 had a depth d of the recessed flat surface region of 0.8 mm. The tire of Comparative Example 1 was not provided with a recessed flat surface region.

Test tires had a tire size of 195/65R15 (load: 5 kN, air pressure: 150 kPa). An attached object (housing) that stored an electronic circuit including an air pressure sensor and a transmitter, 100 g in weight, was attached to a tread portion of the tire inner surface in the state illustrated in FIG. 7B, and rotation of the housing was observed during travel using a drum testing machine (travel speed: 80 km/hr, travel time: 20 hours).

The results from examining each of the test tires for the presence/absence of rotation, a radio wave reception rate, and the presence/absence of housing damage are as shown in Table 1.

All of the samples of both Working Examples 1 and 2 showed excellent prevention of the occurrence of rotation and, according to Working Examples 1 and 2, exhibited a high radio wave reception rate and no housing damage. The samples of Comparative Example 1 were found to have a low radio wave reception rate as well as housing damage and wear, and thus could not be considered favorable.

According to the present technology, in a pneumatic tire having an object with specific functionality attached to an inner surface of the pneumatic tire using a mechanical fastener member, the object with the specific function attached by the mechanical fastener member can be effectively prevented from executing rotating motion about the mechanical fastener member as a rotation central axis as the pneumatic tire rolls. As a result, it is possible to use the specific function of the object with favorable durability and accuracy.

TABLE 1

|  | Comparative Example 1 | Working Example 1 | Working Example 2 |
| --- | --- | --- | --- |
| Collar member | No | Yes | Yes |
| Depth d | 0 | 0.3 mm | 0.8 mm |
| Occurrence of rotation | Yes | Minimal | No |
| Radio wave reception rate | 54% | 83% | 92% |
| Housing damage | Housing wear Yes | No | No |

The invention claimed is:

1. A pneumatic tire, comprising:
    a mechanical fastener member on a tire inner surface, the mechanical fastener member corresponding to a first member of a mechanical fastener separable into two members,
    a recessed flat surface region being formed on the tire inner surface around the mechanical fastener member as a recessed portion having a step from peripheral portions of the recessed portion;
    wherein a profile shape of the recessed flat surface region is asymmetrical with respect to one and/or both of a line in a tire axial direction and a line in a tire circumferential direction that pass through the center of the mechanical fastener member in a plan view of the tire inner surface from the vertical direction.

2. The pneumatic tire according to claim 1, wherein the step is at least 0.5 mm in a vertical direction of the tire inner surface, and a distance between a center of the mechanical fastener member and a profile line of the recessed flat surface region is not constant but changes in a plan view of the tire inner surface from the vertical direction.

3. The pneumatic tire according to claim 2, wherein the profile shape of the recessed flat surface region is configured by curved lines having a radius of curvature of at least 2 mm or straight lines, without having sharp corners, in a plan view of the tire inner surface from the vertical direction.

4. The pneumatic tire according to claim 3, wherein the profile shape of the recessed flat surface region is symmetrical with respect to at least one axis of orthogonal coordinates in a tire circumferential direction and a tire axial direction about the mechanical fastener member as the center, and is a shape configured by substantially arcuate shapes and straight lines, in a plan view of the tire inner surface from the vertical direction.

5. The pneumatic tire according to claim 4, further comprising an attached object having a second member of the mechanical fastener that engages with the first member of the mechanical fastener on the tire inner surface, the object being fixed on the tire inner surface by engaging the two members.

6. The pneumatic tire according to claim 5, wherein a rotatable angle of the attached object about the mechanical fastener member as a central axis is 10 degrees or less in a plan view of the tire inner surface from the vertical direction.

7. The pneumatic tire according to claim 6, wherein the object provided with the second member is one or a combination of (a) an electronic circuit comprising a sensor, (b) a balance weight, (c) a run-flat core, (d) an object on which an oxygen scavenger, a drying agent, and/or an ultraviolet light detecting color fixing agent is applied or mounted, (e) and a noise absorbing member.

8. The pneumatic tire according to claim 1, wherein the profile shape of the recessed flat surface region is configured by curved lines having a radius of curvature of at least 2 mm or straight lines, without having sharp corners, in a plan view of the tire inner surface from the vertical direction.

9. The pneumatic tire according to claim 1, wherein the profile shape of the recessed flat surface region is symmetrical with respect to at least one axis of orthogonal coordinates in a tire circumferential direction and a tire axial direction about the mechanical fastener member as the center, and is a shape configured by substantially arcuate shapes and straight lines, in a plan view of the tire inner surface from the vertical direction.

10. The pneumatic tire according to claim 1, further comprising an attached object having a second member of the mechanical fastener that engages with the first member of the mechanical fastener on the tire inner surface, the object being fixed on the tire inner surface by engaging the two members.

11. The pneumatic tire according to claim 10, wherein a rotatable angle of the attached object about the mechanical fastener member as a central axis is 10 degrees or less in a plan view of the tire inner surface from the vertical direction.

12. The pneumatic tire according to claim 10, wherein the object provided with the second member is one or a combination of (a) an electronic circuit comprising a sensor, (b) a balance weight, (c) a run-flat core, (d) an object on which an oxygen scavenger, a drying agent, and/or an ultraviolet light detecting color fixing agent is applied or mounted, (e) and a noise absorbing member.

* * * * *